US010758392B2

(12) United States Patent
Mason et al.

(10) Patent No.: US 10,758,392 B2
(45) Date of Patent: Sep. 1, 2020

(54) FLEXION AND EXTENSION RANGE LIMITING HINGE FOR AN ORTHOPEDIC BRACE

(71) Applicant: United Surgical, Inc., Ft. Wayne, IN (US)

(72) Inventors: Jeffrey T. Mason, Escondido, CA (US); Jerome Yoder, Ft. Wayne, IN (US)

(73) Assignee: United Surgical, Inc., Ft. Wayne, IN (US)

( * ) Notice: Subject to any disclaimer, the term of this patent is extended or adjusted under 35 U.S.C. 154(b) by 545 days.

(21) Appl. No.: 15/608,599

(22) Filed: May 30, 2017

(65) Prior Publication Data

US 2017/0340471 A1 Nov. 30, 2017

Related U.S. Application Data

(60) Provisional application No. 62/343,568, filed on May 31, 2016.

(51) Int. Cl.
*A61F 5/01* (2006.01)

(52) U.S. Cl.
CPC ............. *A61F 5/0123* (2013.01); *A61F 5/01* (2013.01); *A61F 2005/0139* (2013.01); *A61F 2005/0158* (2013.01); *A61F 2005/0167* (2013.01)

(58) Field of Classification Search
CPC ........ A61F 5/01; A61F 5/0102; A61F 5/0123; A61F 5/0118; A61F 5/013; A61F 2005/0132; A61F 2005/0137; A61F 2005/0139; A61F 2005/0158; A61F 2005/0165; A61F 2005/0167

USPC ...................................... 602/1, 5, 16, 23, 26
See application file for complete search history.

(56) References Cited

U.S. PATENT DOCUMENTS

| 4,493,316 A | 1/1985 | Reed et al. |
| 4,697,583 A | 10/1987 | Mason et al. |
| 4,732,143 A | 3/1988 | Kausek et al. |
| 4,966,133 A | 10/1990 | Kausek |
| 5,661,596 A | 9/1997 | Young |

(Continued)

FOREIGN PATENT DOCUMENTS

| DE | 202011102331 U1 * | 8/2011 | ........... A61F 5/0123 |
| DE | 202011102331 U1 | 10/2011 | |

(Continued)

*Primary Examiner* — Tarla R Patel
(74) *Attorney, Agent, or Firm* — Felix L. Fischer

(57) ABSTRACT

An angle limitation system for an orthopedic brace employs a hinge assembly rotatably receiving an upper strut and a lower strut and having a hinge plate and a hinge assembly cap. An extension angle limit element is removably insertable in an anterior port between the hinge plate and hinge assembly cap. The extension angle limit element has a body with limiting surfaces adapted to engage mating faces indented in the anterior edges of the upper and lower strut. A flexion angle limit element is removably insertable in a posterior port between the hinge plate and hinge assembly cap. The flexion angle limit element has a body with limiting surfaces adapted to engage mating faces indented in the posterior edges of the upper and lower strut. Engagement mechanisms are adapted to releasably secure the flexion angle limit element in the posterior port and the engagement angle limit element in the anterior port.

9 Claims, 17 Drawing Sheets

(56) References Cited

U.S. PATENT DOCUMENTS

| | | | | |
|---|---|---|---|---|
| 5,772,618 A | * | 6/1998 | Mason | A61F 5/0123 602/16 |
| 7,320,672 B2 | * | 1/2008 | Turrini | A61F 5/0123 602/16 |
| 7,488,300 B2 | * | 2/2009 | Houser | A61F 5/0123 16/325 |
| 8,157,756 B2 | | 4/2012 | Schimek et al. | |
| 8,920,349 B2 | * | 12/2014 | Ferrigolo | A61F 5/0123 602/16 |
| 2003/0060745 A1 | | 3/2003 | Seligman | |
| 2003/0149386 A1 | | 8/2003 | Ceriani et al. | |
| 2003/0156856 A1 | | 8/2003 | Seligman et al. | |
| 2004/0049140 A1 | | 3/2004 | Doty et al. | |
| 2004/0067095 A1 | | 4/2004 | Pansiera | |
| 2006/0173392 A1 | | 8/2006 | Turrini et al. | |
| 2007/0276305 A1 | | 11/2007 | Kahlmeyer et al. | |
| 2008/0082031 A1 | * | 4/2008 | Nathanson | A61F 5/0123 602/16 |
| 2015/0223958 A1 | | 8/2015 | Dunn | |
| 2016/0058596 A1 | * | 3/2016 | Chiang | A61F 5/0123 602/16 |

FOREIGN PATENT DOCUMENTS

| | | |
|---|---|---|
| DE | 202015003755 U1 | 7/2015 |
| EP | 2124850 B1 | 12/2010 |
| EP | 2526906 A1 | 11/2012 |

\* cited by examiner

FLEXION AND EXTENSION RANGE LIMITING HINGE FOR AN ORTHOPEDIC BRACE

REFERENCE TO RELATED APPLICATIONS

This application claims priority of U.S. provisional application Ser. No. 62/343,568 filed on May 31, 2016 entitled FLEXION AND EXTENSION RANGE LIMITING HINGE FOR AN ORTHOPEDIC BRACE and having a common assignee with the present invention, the disclosure of which is incorporated herein by reference.

BACKGROUND INFORMATION

Field

Embodiments of the disclosure relate generally to the field of anatomical support braces and more particularly to a system for limiting the range of flexion and extension in a brace hinge including a flexion angle limit element removably insertable on a first side of the hinge body and an extension angle limit element removably insertable on a second side of the hinge body, each of the extension angle limit element and flexion angle limit element each have two limiting faces which engage supporting struts.

Background

Orthopedic braces are used for various treatment and prophylactic purposes. For knee braces, particular uses may require incorporating an angle limiting function to resist knee flexion or extension past certain levels. Users may require multiple angles of limitation during the use of an orthopedic knee brace. Users prefer that the angle limiting system be adjustable for different angles It is therefore desirable to provide a system for adjusting the flexion and extension limiting system rapidly and easily.

SUMMARY

Embodiments disclosed herein provide an angle limitation system for an orthopedic brace having a hinge assembly rotatably receiving an upper strut and a lower strut and having a hinge plate and a hinge assembly cap. An extension angle limit element is removably insertable in an anterior port between the hinge plate and hinge assembly cap. The extension angle limit element has a body with limiting surfaces adapted to engage mating faces indented in the anterior edges of the upper and lower strut. A flexion angle limit element is removably insertable in a posterior port between the hinge plate and hinge assembly cap. The flexion angle limit element has a body with limiting surfaces adapted to engage mating faces indented in the posterior edges of the upper and lower strut. Engagement mechanisms are adapted to releasably secure the flexion angle limit element in the posterior port and the engagement angle limit element in the anterior port.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide an angle limitation system for an orthopedic brace having a flexion angle limit element removably insertable on a posterior side of the hinge body and an extension angle limit element removably insertable on an anterior side of the hinge body. The extension angle limit element and flexion angle limit element are received in ports in the hinge body formed between a hinge plate and hinge assembly cap. Each angle limit element has two limiting surfaces which engage mating faces on the supporting struts of the brace to limit extension angle and flexion angle respectively. Engagement mechanisms adapted to secure the angle limit elements in the ports are provided. In a first embodiment for the engagement mechanism, the angle limit elements are held in place with a flexible strut or tab on the angle limit element received in a mating channel in a bottom surface of the hinge assembly cap. The angle limit elements are removable by depressing the strut with a tool inserted through apertures in the hinge assembly cap into the channel. A second embodiment of the engagement mechanism provides for jaws on the angle limit element with a releasable button received in a cylindrical cutout in the jaws to restrain the angle limit element in the port. In a third embodiment the angle limit elements are restrained in the port by flexible jaws engaging a catch post. The angle limit elements are insertable and removable without disassembly of the hinge elements or removal of the brace from the patient. Selectable angle limit elements with limiting surfaces having differing total angle may be removably inserted into the ports to vary either the extension angle or the flexion angle.

Figure 1A:
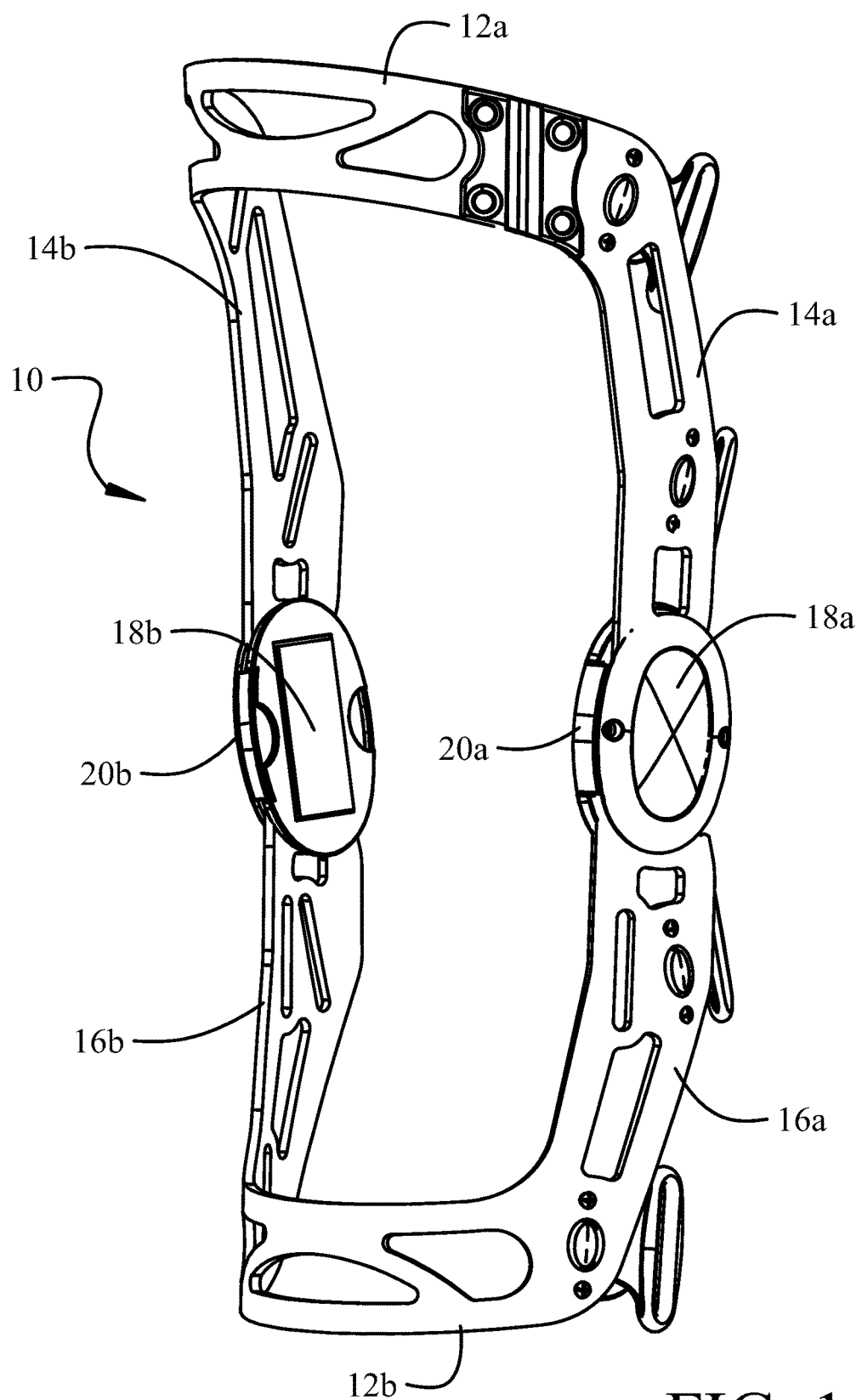
FIG. 1A is a front perspective view of an orthopedic brace configured to incorporate the embodiments disclosed herein.
Figure 1B:
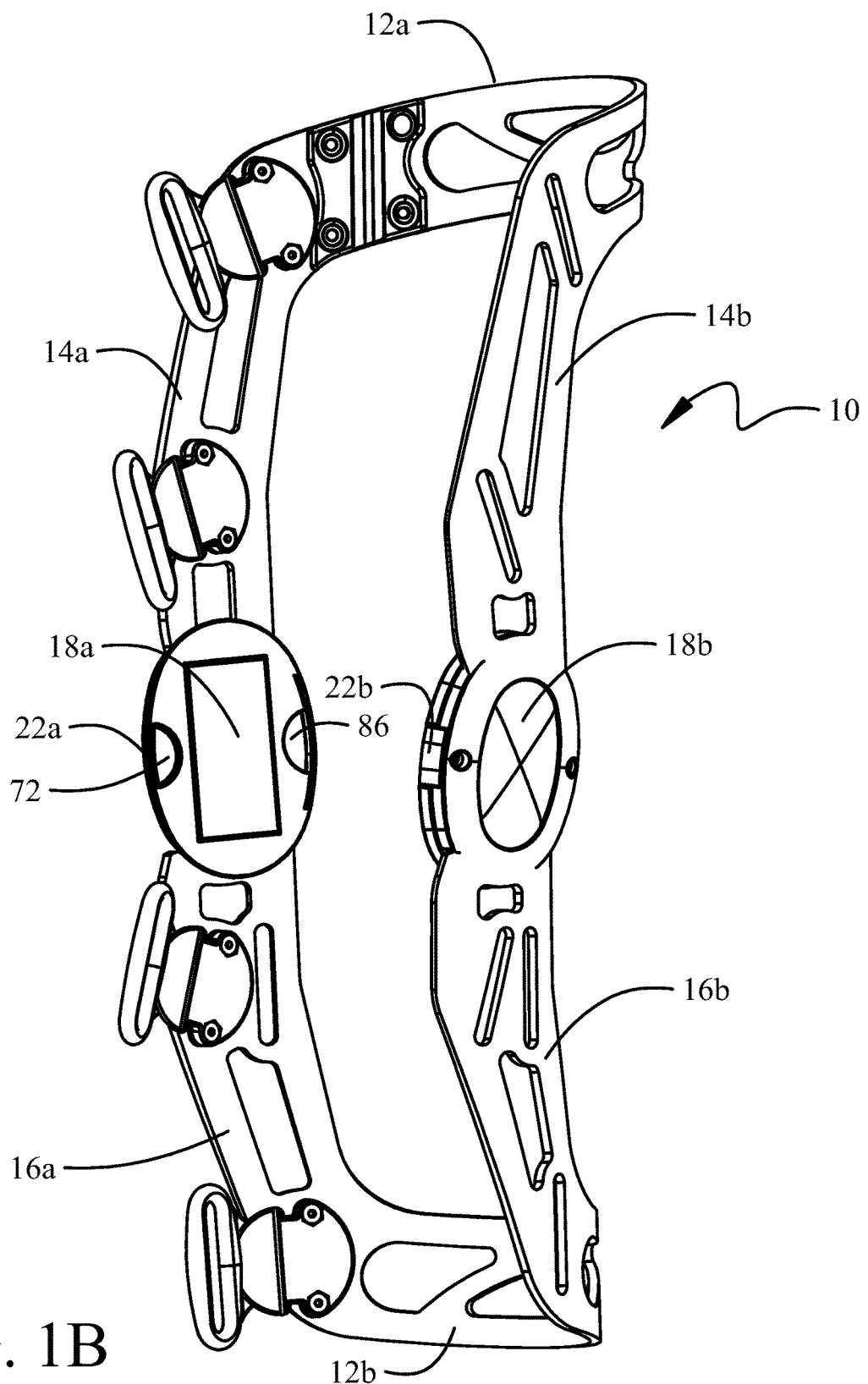
FIG. 1B is a rear perspective view of the brace of FIG. 1A.

Referring to the drawings, FIGS. 1A and 1B show an exemplary orthopedic brace 10 incorporating upper and lower support cuffs 12a, 12b to engage the thigh and shin of a user. Upper support struts 14a and 14b extend downward from the upper support cuff 12a and lower support struts 16a and 16b extend upward from the lower support cuff 12b. The upper and lower support struts are engaged in hinge assemblies 18a and 18b. While shown for the embodiments herein as an orthopedic brace for the leg and knee, the embodiments disclosed herein would be equally applicable to braces for other extremities such as the arm and elbow.

For disclosure of position, surface tabs for flexion and extension angle limit elements engaged in the hinge assemblies, as will be described in greater detail subsequently, are shown in FIGS. 1A and 1B. Extension angle limit elements have surface tabs 20a and 20b while flexion angle limit elements have surface tabs 22a and 22b.

Figure 2A:
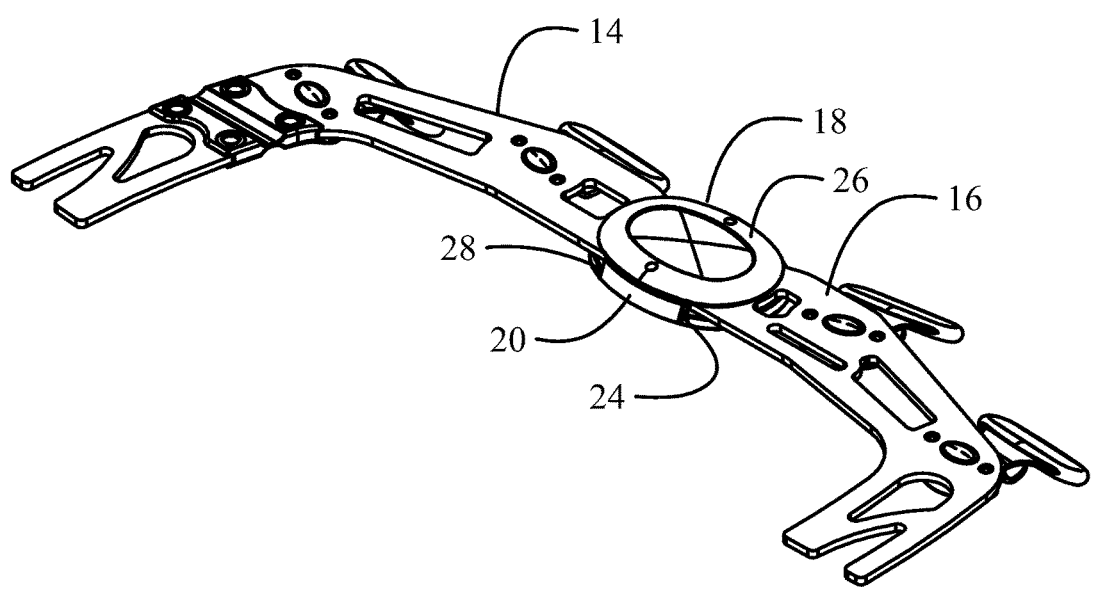
FIG. 2A is a front perspective view of one of the support struts and hinge assembly of the brace.
Figure 2B:
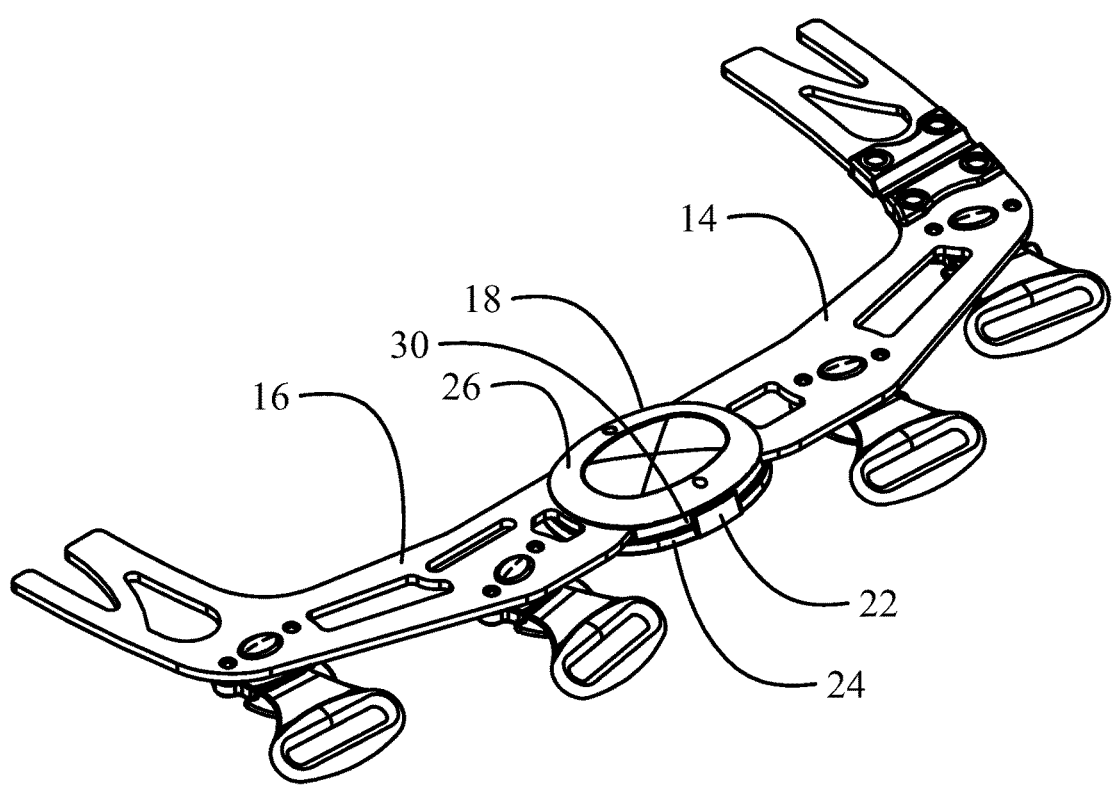
FIG. 2B is a rear perspective view of one of the support struts and hinge assembly of the brace.

The hinge assemblies and struts of one medial or lateral side of the brace are shown in detail in FIGS. 2A and 2B. The upper strut 14 and lower strut 16 are received in the hinge assembly 18. The hinge assembly 18 has a hinge plate 24 and a hinge assembly cap 26. An extension angle limit element having surface tab 20 is received in an anterior port 28 between the hinge plate 24 and hinge assembly cap 26 (seen in FIG. 2A) in the hinge assembly 18. A flexion angle limit element having surface tab 22 is received in a posterior port 30 between the hinge plate 24 and hinge assembly cap 26 (seen in FIG. 2B in the hinge assembly 18.

Figure 2C:
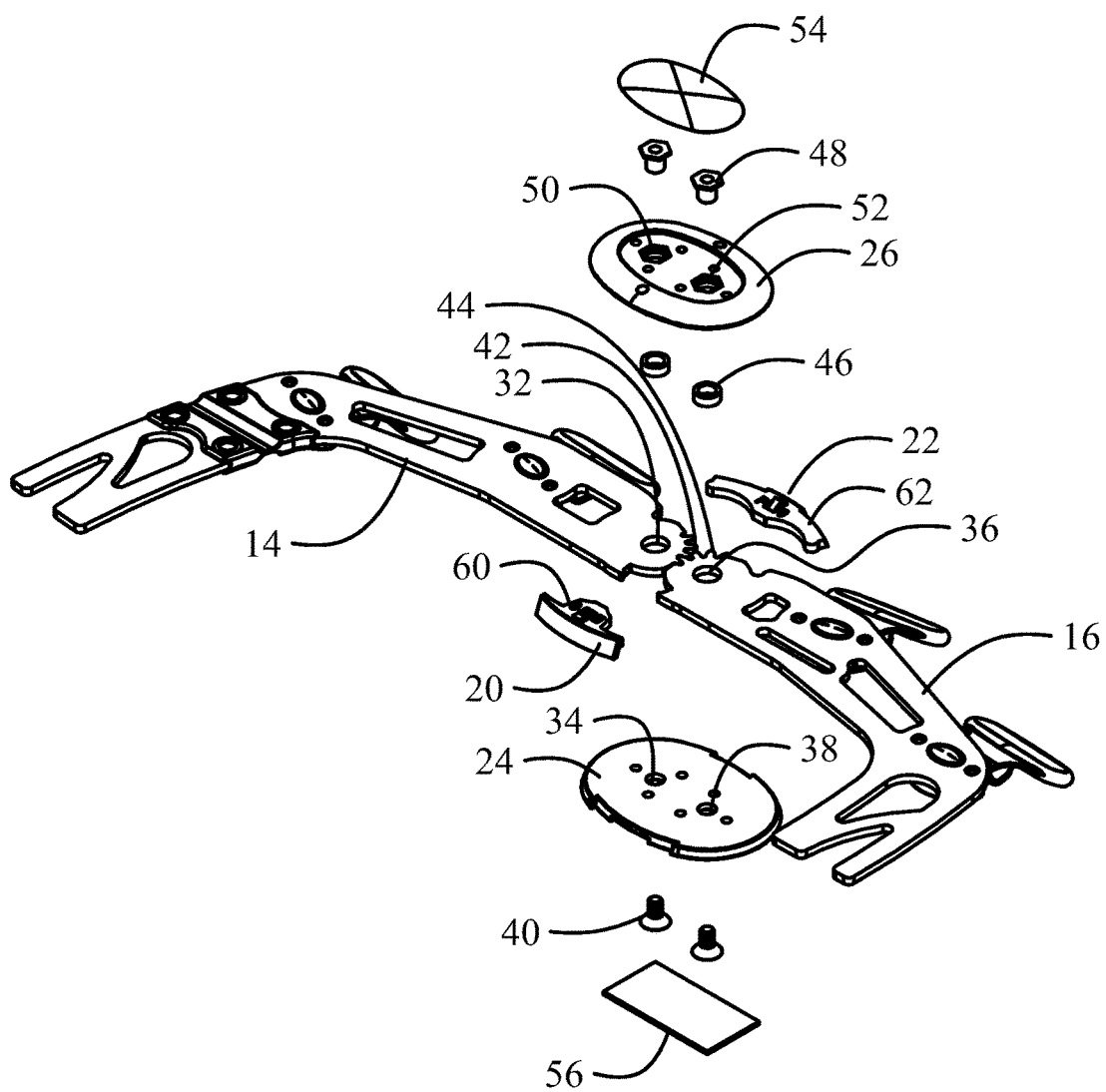
FIG. 2C is an exploded front perspective view of one of the support struts and hinge assembly of the brace with a first embodiment of the angle limit elements and the associated securing system.

Seen in the exploded view of FIG. 2C for an exemplary embodiment, the upper strut 14 has an upper pivot hole 32 which is aligned with an upper axle bore 34 on the hinge plate 24 and the lower strut 16 has a lower pivot hole 36 which is aligned with a lower axle bore 38 on the hinge plate. Bolts 40 are received through the upper and lower axle bores and upper and lower pivot holes to act as rotational axles for the flexion and extension of the brace struts. Gear teeth 42 and 44 on the upper and lower struts respectively are engaged to coordinate rotation of the struts in the hinge assembly. Bushings 46 may be engaged in the pivot holes to facilitate smooth rotation and securing nuts 48 engage the bolts 40 through upper and lower exterior bores 50 and 52 in the hinge assembly cap 26. An outer cover 54 may be employed to mask the securing nuts in the hinge assembly cap and an inner cover 56 may be employed to mask the bolts 40 in the hinge plate 24. Extension angle limit element 60 and flexion angle limit element 62 are seen in FIG. 2C.

Figure 2D:
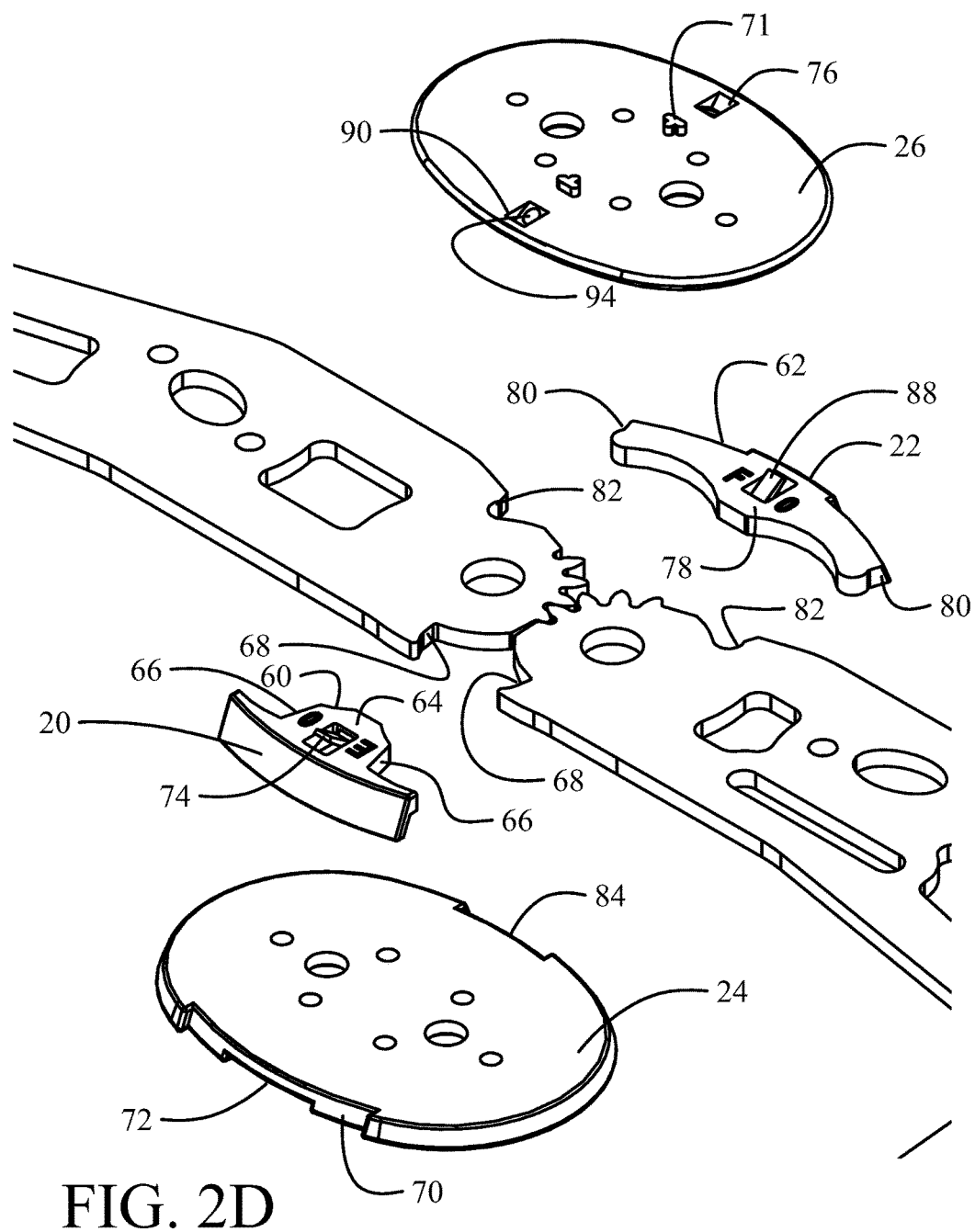
FIG. 2D is a detailed exploded front perspective view of one of the support struts and hinge assembly of the brace with the first embodiment of the angle limit elements and the associated securing system with the hinge assembly cap inverted to show the engagement reliefs.

Details of a first embodiment for the angle limit elements and the associated engagement mechanisms for retention in the ports are shown in FIG. 2D. The extension angle limit element 60 has a body 64 which includes limiting surfaces 66 which are adapted to be engaged by mating faces 68 indented in anterior edges of the struts 14, 16. The surface tab 20 of the extension angle limit element 60 is received in an anterior recess 70 in the hinge plate 24 when the body of the extension angle limit element is received in the anterior port between the hinge plate and hinge assembly cap 26 (as described with respect to FIG. 2A). Engagement of the surface tab 20 in the recess 70 limits the insertion depth of the extension angle limit element into the port. A raised stop 71 also engages the body to limit insertion depth. A bottom relief 72 (also seen in FIG. 1B) in the recess 70 allows a lower edge of the surface tab 20 to be grasped with a fingernail to assist in removal of the extension angle limit element from the port as will be described subsequently. The extension angle limit element is restrained in the port with a resilient lever 74 extending from the body 64 which is engaged in a mating channel 76 in the hinge assembly cap 26 (shown inverted in FIG. 2D to show the features on the lower surface).

Similarly, the flexion angle limit element 62 has a body 78 which includes limiting surfaces 80 which are adapted to be engaged by mating faces 82 indented in the posterior edges the struts 14, 16. The surface tab 22 of the flexion angle limit element 62 is received in a posterior recess 84 in the hinge plate 24 when the body of the flexion angle limit element is received in the posterior port between the hinge plate and hinge assembly cap 26 (as described with respect to FIG. 2A). Engagement of the surface tab 22 in the recess 84 limits the insertion depth of the flexion angle limit element into the port. A raised stop 85 also engages the body to limit insertion depth. A bottom relief 86 (seen in FIG. 1B) in the recess 70 allows a lower edge of the surface tab 22 to be grasped with a fingernail for removal of the flexion angle limit element from the port. The flexion angle limit element is restrained in the port with a resilient lever 88 extending from the body 64 which is engaged in a mating channel 90 in the hinge assembly cap 26.

Figure 2E:
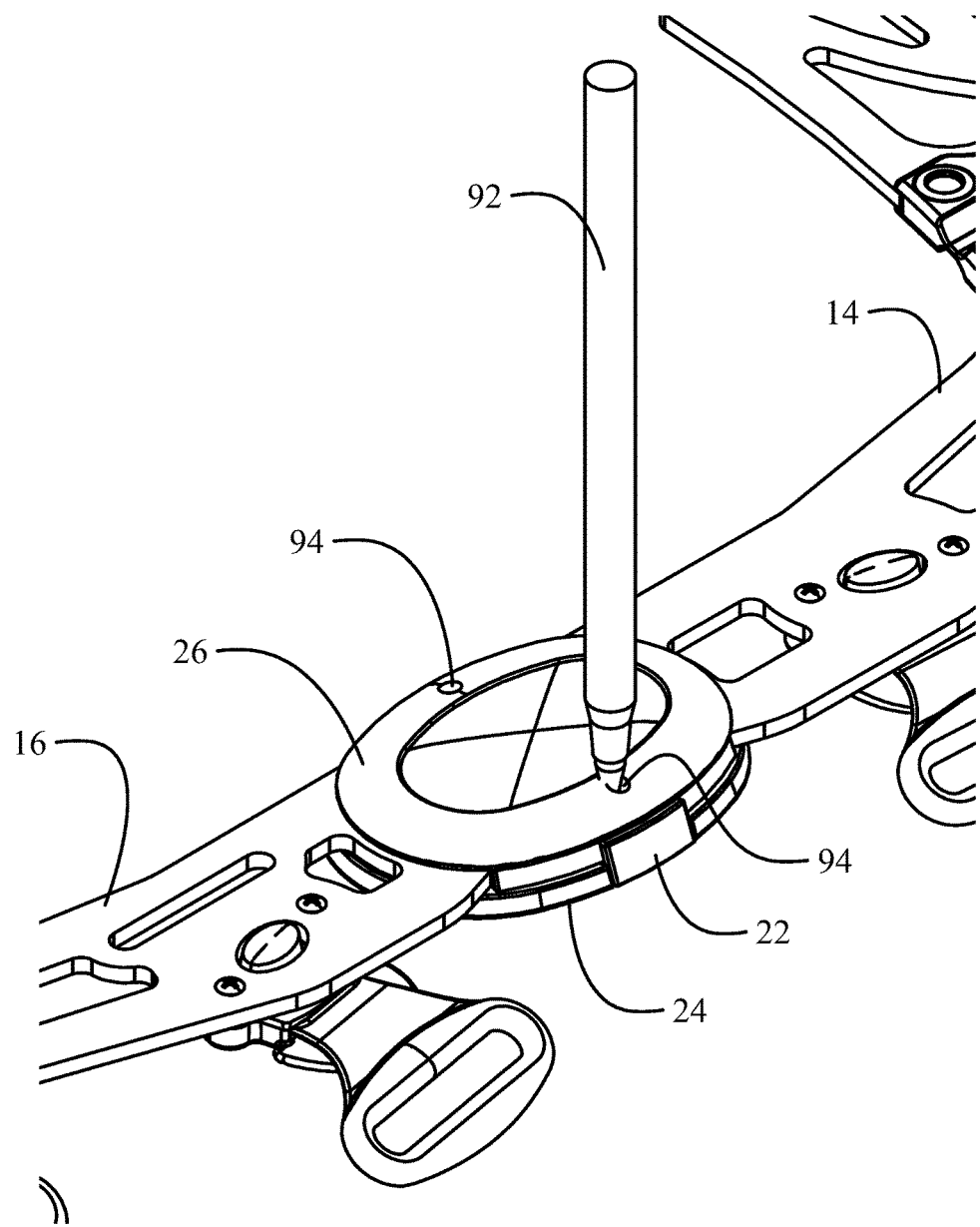
FIG. 2E is a detailed rear perspective view of the hinge assembly and struts with a pen inserted in the disengagement orifice to depress the locking strut on the flexion angle limit element.
Figure 2F:
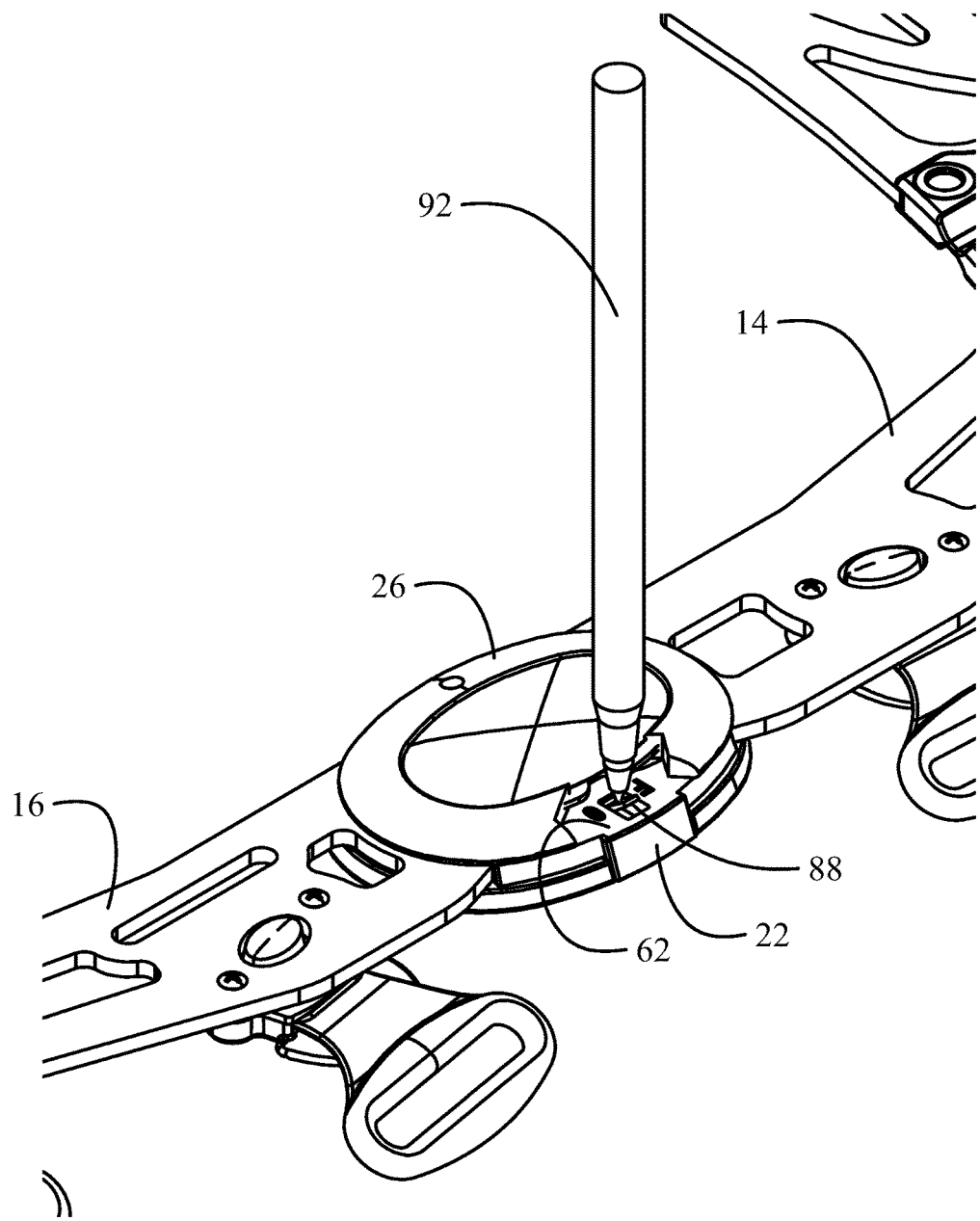
FIG. 2F is a detailed rear perspective view of the hinge assembly and struts with a partial cutaway of the hinge assembly cap to show engagement of the pen to depress the locking strut on the flexion angle limit element.
Figure 2G:
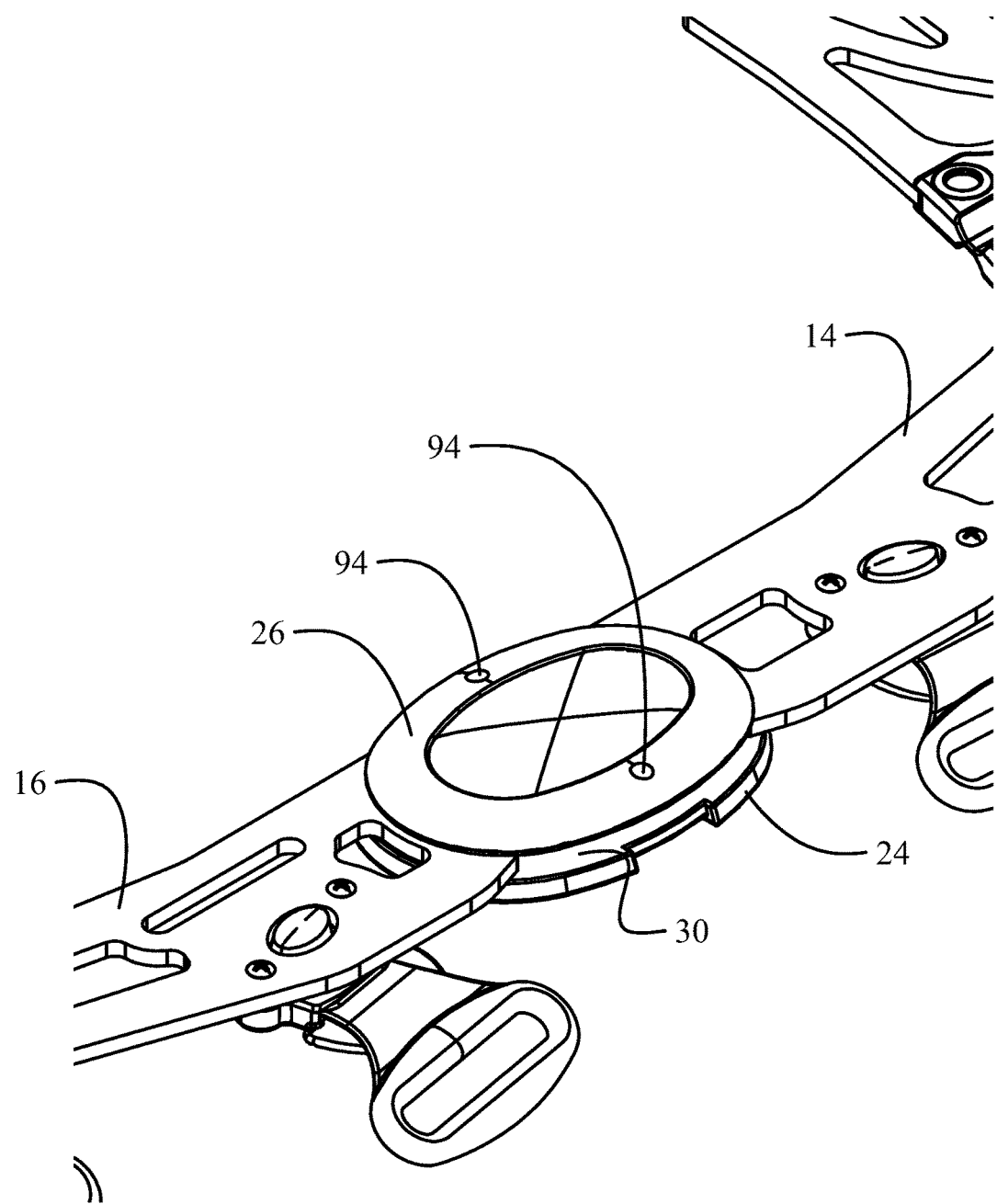
FIG. 2G is a detailed rear perspective view of the hinge assembly and struts as seen in FIGS. 2E and 2F with the flexion angle limit element removed from the posterior port in the hinge assembly.

When the extension angle limit element 60 and flexion angle limit element 62 are received in their respective ports the levers 74 and 88 engaged in the mating channels 76 and 90 prevent extraction of the angle limit elements. To extract an angle limit element from the brace for replacement with an angle limit element having a different angle or to provide free movement of the brace, a pen 92 or similar pointed tool, is inserted through an aperture 94 extending through the hinge assembly cap 26 into the associated channel; using the flexion angle limit element as an example as shown in FIG. 2E, channel 90 for the flexion angle limit element. The pen 92 depresses the lever 88 to clear the channel 90 as shown in FIG. 2F allowing the flexion angle limit element 62 to be removed from the port 30 as shown in FIG. 2G.

Figure 3A:
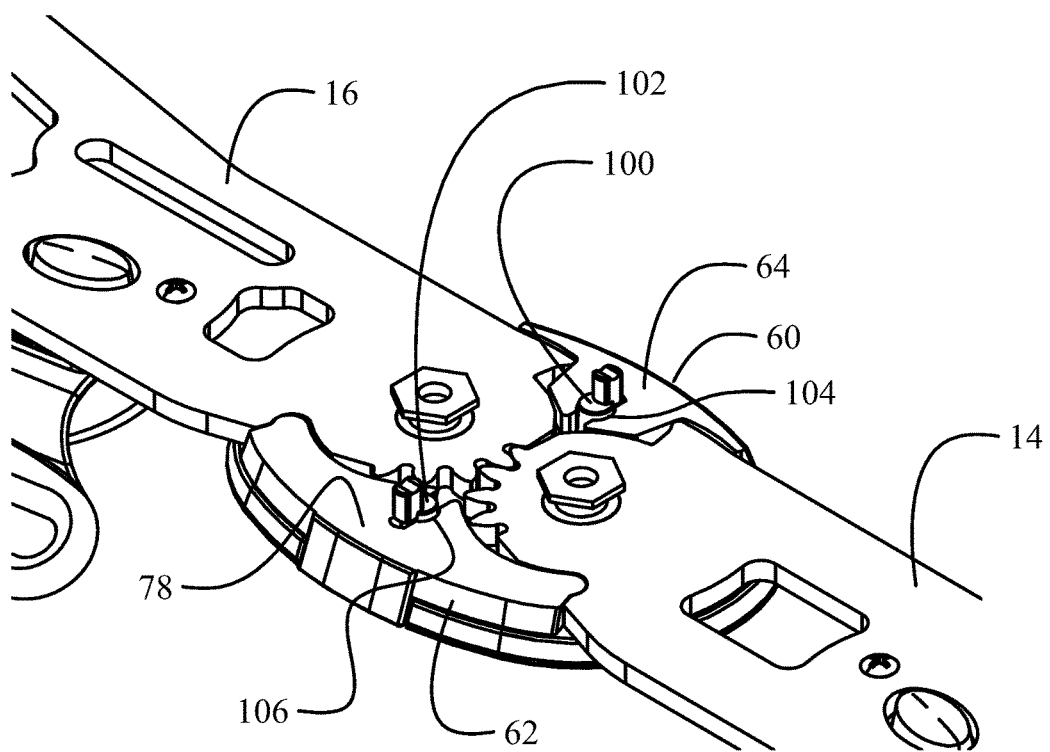
FIG. 3A is a detailed rear perspective view of a second embodiment of the angle limit elements and the associated securing system with the hinge assembly cap removed for clarity.
Figure 3B:
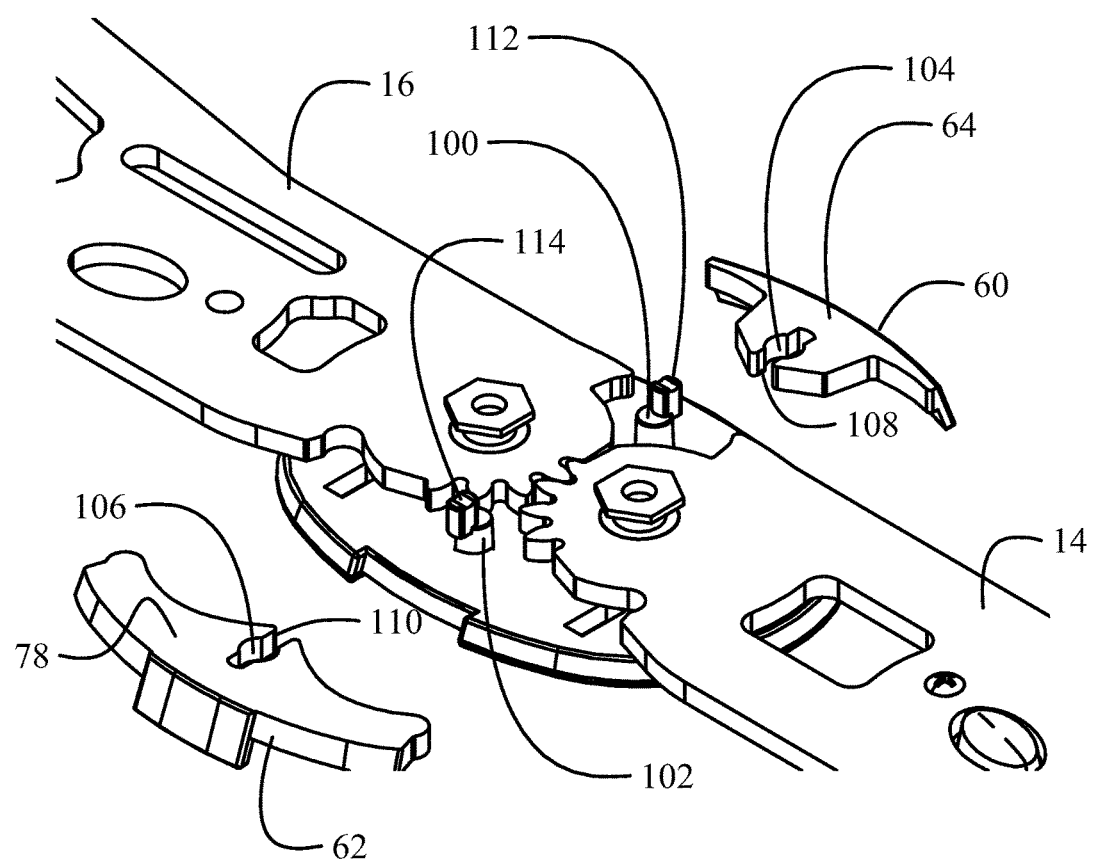
FIG. 3B is a detailed rear perspective view of the second embodiment of the angle limit elements and the associated securing system with the hinge assembly cap removed and the angle limit elements removed to show the catch buttons.

A second embodiment is shown in FIGS. 3A and 3B with the hinge assembly cap removed wherein the extension and flexion angle limit elements 62 and 64 are constrained in the ports in the hinge assembly with cylindrical buttons 100 and 102 received in cylindrical cutouts 104 and 106 in the bodies 64 and 78 respectively. Channels 108 and 110 cut into the bodies 64 and 78 transecting the cylindrical cutouts 104 and 106. Buttons 100 and 102 are depressible into the hinge plate 26 by engaging extending tabs 112 and 114 with the pen 92 or similar tool extending through apertures 94 in the hinge assembly cap (as described with respect to FIG. 2E). The transecting channels 108 and 110 are sized for clearance with the tabs 112 and 114 to allow insertion or extraction of the angle limit elements from the hinge assembly ports when the buttons are depressed.

Figure 4A:
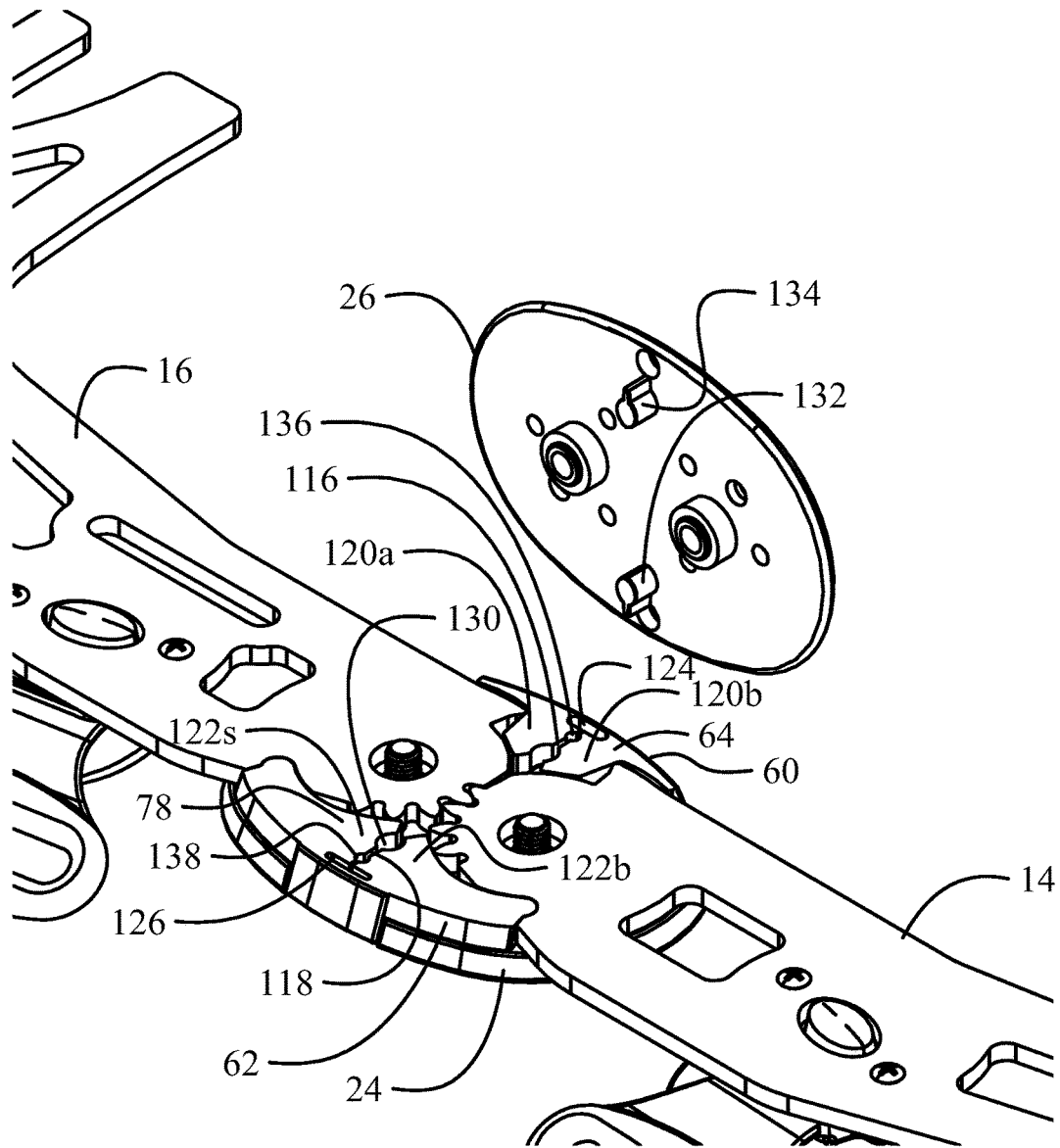
FIG. 4A is a detailed rear perspective view of a third embodiment of the angle limit elements and the associated securing system with the hinge assembly cap exploded and rotated 90° to show the catch posts.
Figure 4B:
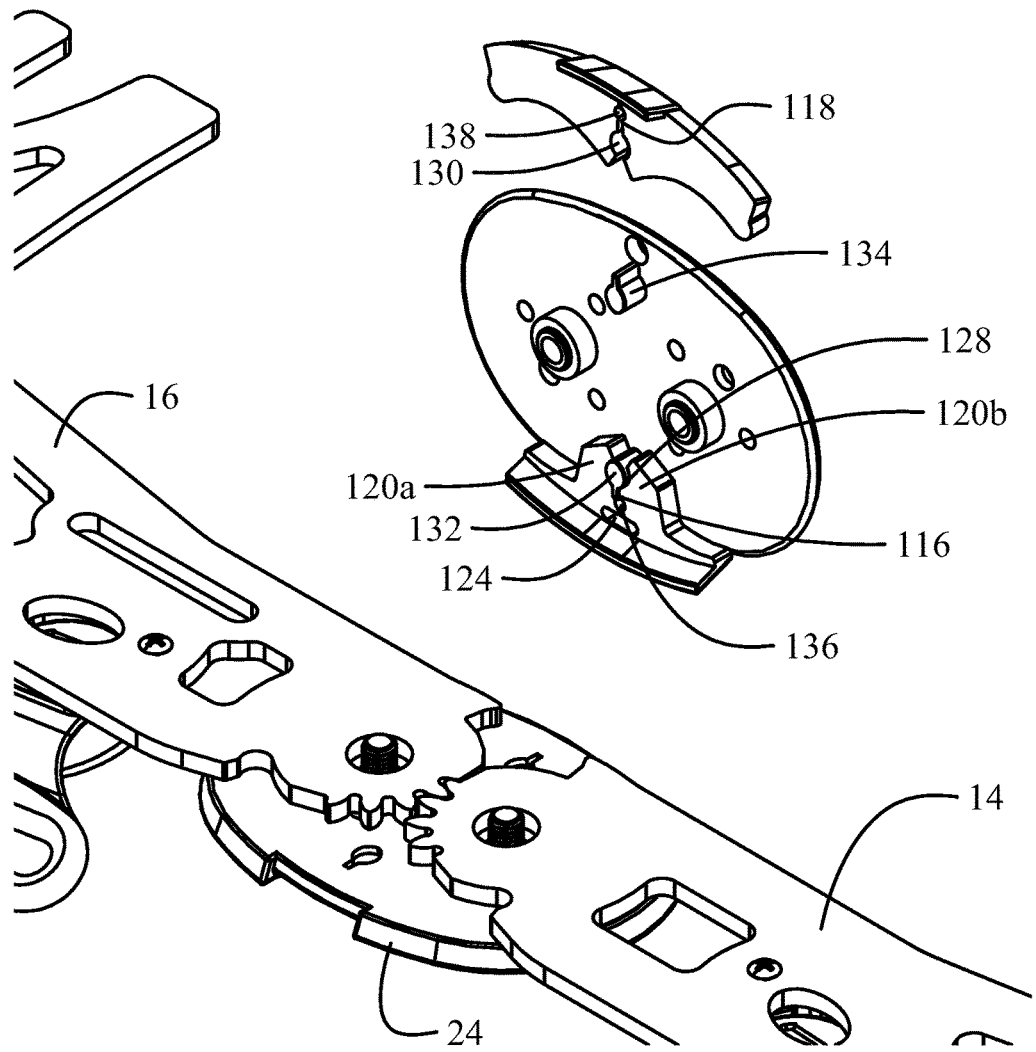
FIG. 4B is a detailed rear perspective view of the third embodiment of the angle limit elements and the associated securing system with the hinge assembly cap exploded and rotated 90° and the extension angle limit element engaged to the associated catch post and the flexion angle limit element disengaged from the catch post.

A third embodiment is shown in FIGS. 4A and 4B with the hinge assembly cap 26 rotated 90° to show features on the lower surface. The bodies 64 and 78 of the extension and flexion angle limit elements 60 and 62 are substantially bifurcated with capped slots 116 and 118 to form flexible jaw pairs 120a, 120b and 122a, 122b. The capped slots have transverse reliefs 124 and 126 and substantially cylindrical indentations 128 and 130. The cylindrical indentations of the jaws resiliently receive restraining posts 132 and 134 which depend from a lower surface of the hinge assembly cap 26 (or in alternative embodiments extend from an upper surface of the hinge plate 24) to extend between the hinge plate and hinge assembly cap. The jaw pairs are sufficiently flexible to allow insertion and extraction of the angle limit elements from the ports in the hinge assembly. However, key holes 136 and 138 may be present proximate the transverse reliefs to allow insertion of the pen 92 through apertures 94 to urge the jaw pairs apart to more easily extract the angle limit elements.

Figure 5A:
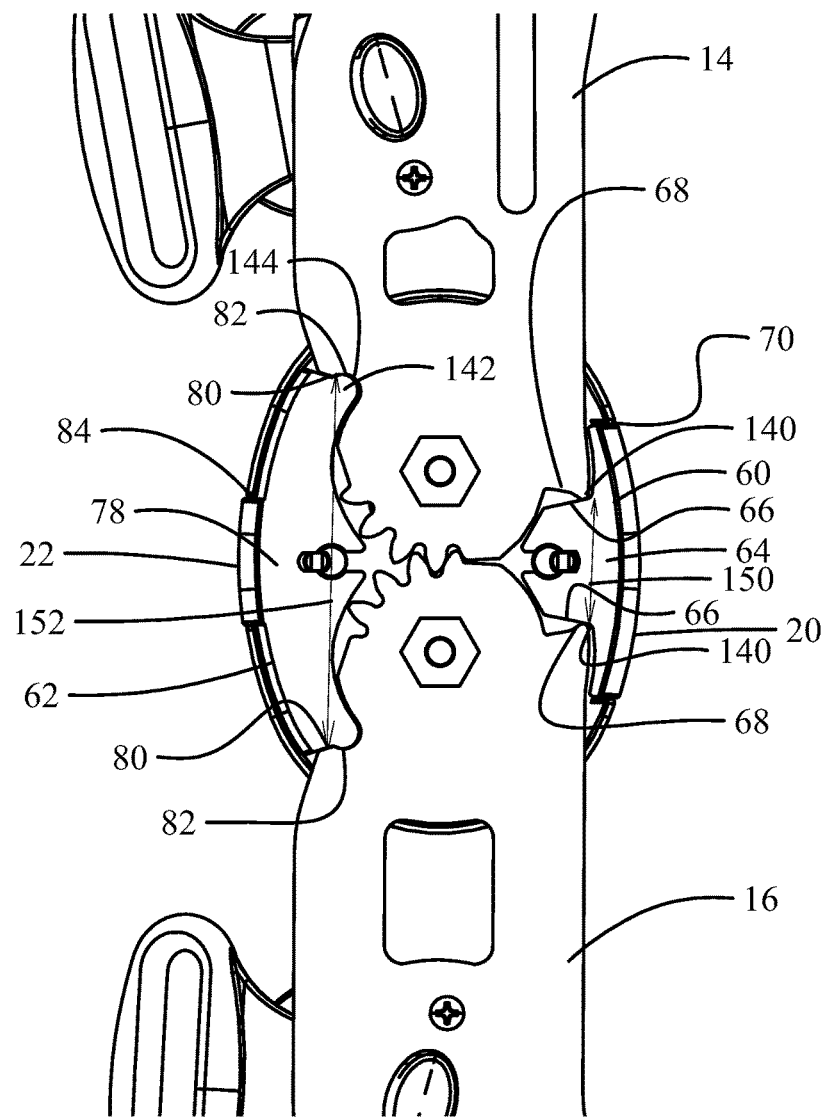
FIG. 5A is a detailed side view of the second embodiment with the hinge assembly cap removed showing flexion and extension angle limit elements sized to lock the brace struts at a zero flexion and zero extension angle.

For any of the restraining embodiments described, operation of the extension and flexion angle limit elements in the brace is substantially identical. FIG. 5A shows and example of angle limit elements sized to constrain the brace at 0° for both extension and flexion. For the extension angle limit element 60, limiting surfaces 66 are located at the vertical extents of body 64 and are adapted to be engaged by mating faces 68 indented in the anterior surfaces of the struts 14, 16. As previously described, the surface tab 20 is received in the recess 70 in the hinge plate 24 when the body of the extension angle limit element is received in the anterior port between the hinge plate and hinge assembly cap 26. Sizing of the surface tab 20 to be received the anterior recess 70 assures that a proper extension angle limit element is installed in the anterior port. Shaping of the limiting surfaces 66 and the mating faces 68 is made to employ the mechanical leverage present in the rotation of the struts in extension to prevent the extension angle limit element from being squeezed out of the port as the struts reach the constrained extension angle. Points 140 in the mating faces 68 engage the limiting surfaces 66 to provide a clamping effect urging the extension angle element inward with extension pressure.

Similarly, for the flexion angle limit element 62 limiting surfaces 80 are located at the vertical extents of body 78 and are adapted to be engaged by mating faces 82 indented in the posterior surfaces the struts 14, 16. The surface tab 22 of the extension angle limit element 62 is received in a recess 84 in the hinge plate 24 when the body of the extension angle limit element is received in the posterior port between the hinge plate and hinge assembly cap 26. Sizing of the surface tab 22 to be received the posterior recess 84 assures that a proper flexion angle limit element is installed in the posterior port. Shaping of the limiting surfaces 80 and the mating faces 82 is again made to employ the mechanical force present in the rotation of the struts in flexion to prevent the flexion angle limit element from being squeezed out of the port as the struts reach at the constrained flexion angle. Rounded protrusions 142 in the limiting surfaces 80 are received in cutouts 144 in the mating faces 82 provide a clamping effect squeezing the flexion angle element for additional restraining effect with flexion pressure.

The width 150 of the body 64 in the extension angle limit element 60 between the limiting surfaces 66 determines the maximum extension angle for rotation of the struts 14, 16. In FIG. 5A the sizing of the extension angle limit element 60 allows rotation of the struts to 0° (full extension). Similarly, the width 152 of the flexion angle limit element 62 between the limiting surfaces 80 determines the maximum flexion angle for rotation of the struts 14, 16. In FIG. 5A the sizing of the flexion angle limit element 62 restricts the struts to 0° of flexion (no flexion). The combination of angle limit elements in FIG. 5A locks the brace at 0°.

Figure 5B:
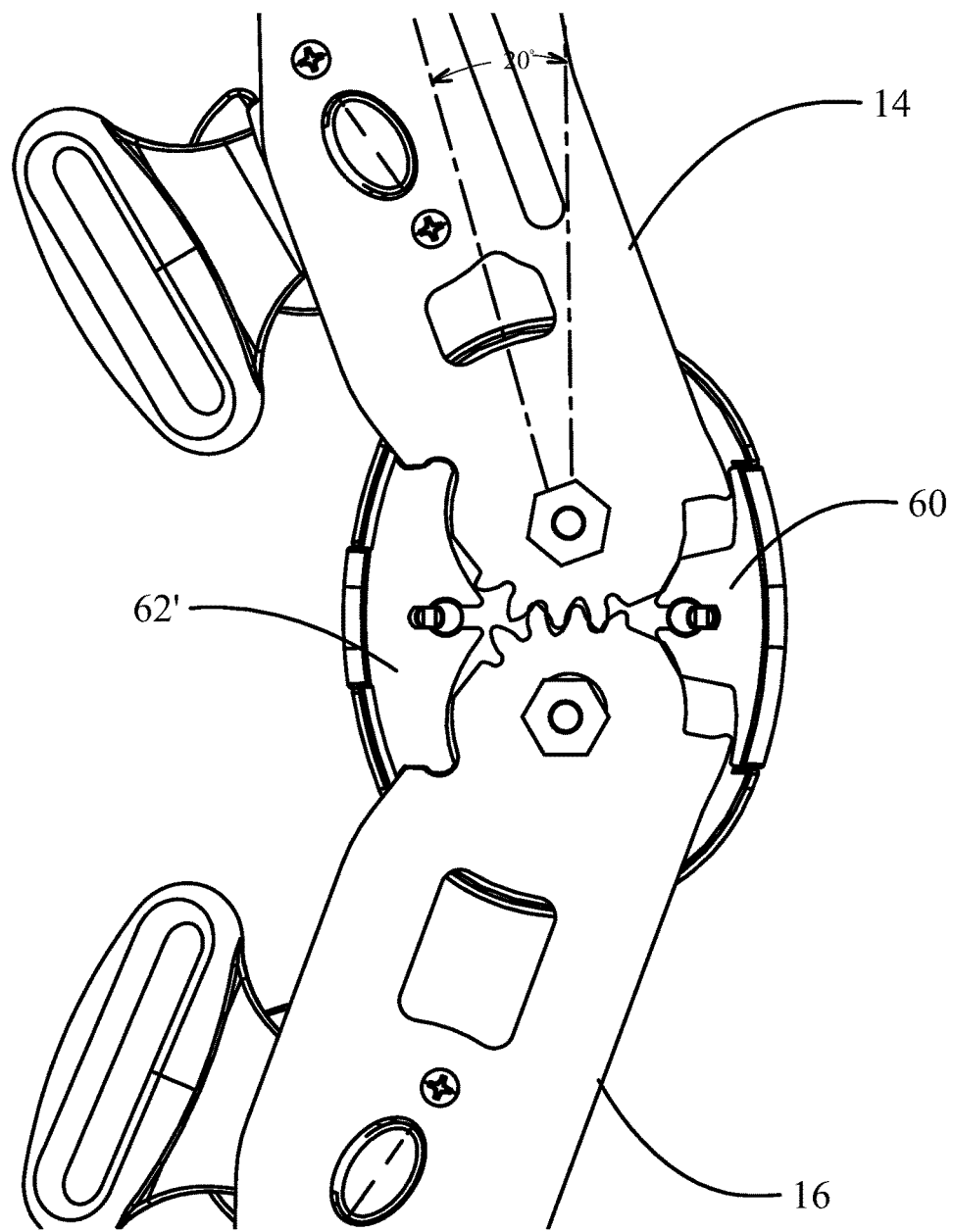
FIG. 5B is a detailed side view of the second embodiment with the hinge assembly cap removed showing the flexion angle limit element sized to allow 20° of flexion in the brace struts and the extension angle limit element sized for zero extension angle.
Figure 5C:
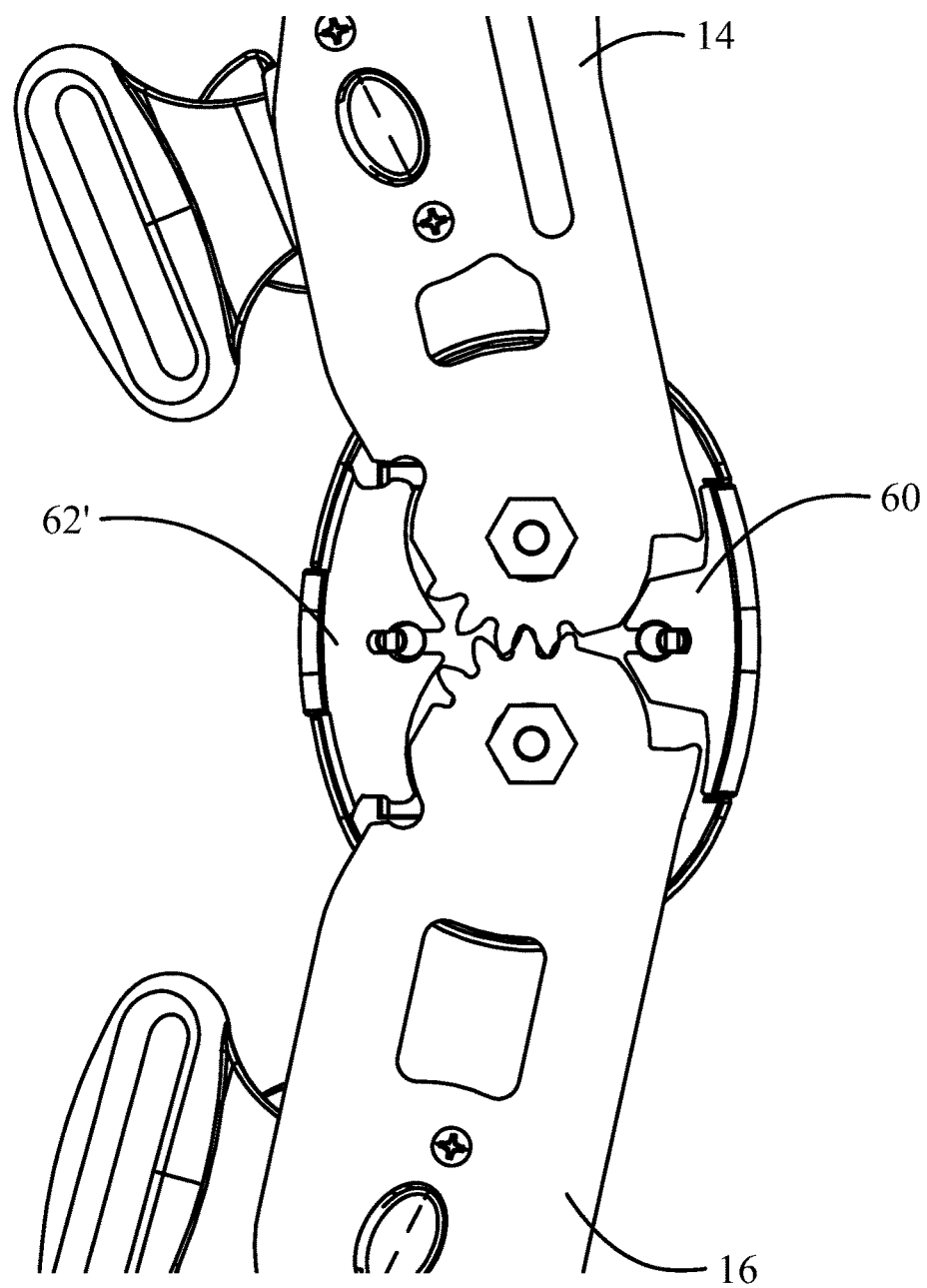
FIG. 5C is a detailed side view of the second embodiment with the hinge assembly cap removed and the 20° flexion angle limit element and 0° extension angle limit element of FIG. 5B but with the brace flexed at 15° to demonstrate the freedom of movement between the limiting angles; and, FIG. 5D is a detailed side view of the second embodiment with the hinge assembly cap removed showing the flexion angle limit element sized to allow 20° of flexion in the brace struts and the extension angle limit element sized for limiting extension angle at 15°.
Figure 5D:
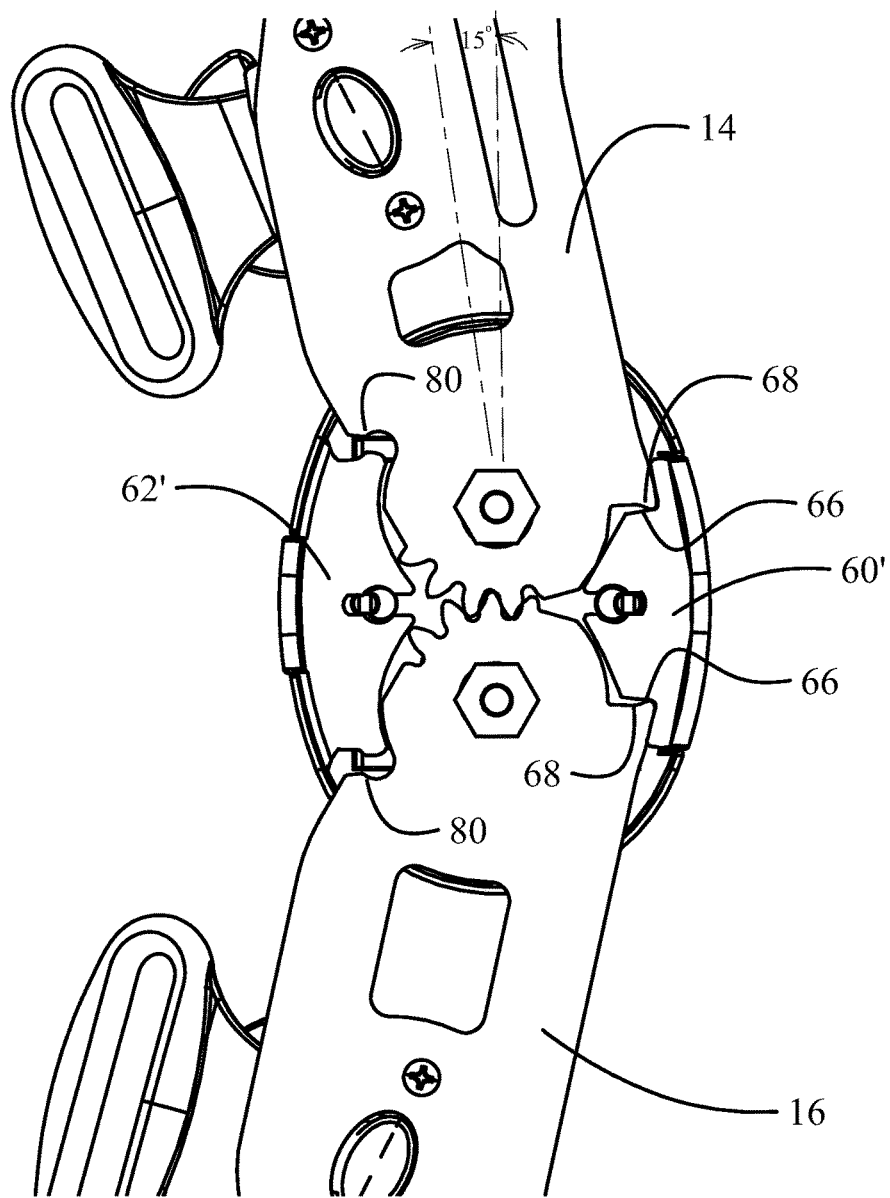

In FIG. 5B, the flexion angle limit element 62 has been replaced with a flexion angle limit element 62' with reduced width to allow 20° of flexion and the brace is shown at the flexion limit. FIG. 5C shows the brace with flexion angle limit element 62' inserted in the posterior port and the struts positioned at a flexion angle of 15° demonstrating freedom of rotation of the struts between 0° and 20°. FIG. 5D shows the brace with extension angle limit element 60 replaced with an extension angle limit element 60' in the anterior port wherein the extension angle limit element 60' has an increased width to limit extension to 15°. In FIG. 5D the brace is shown at the limited extension angle with mating surfaces 68 in contact with the limiting surfaces 66. Flexion angle limit element 62' is not yet engaged by the mating surfaces 80 in the struts and is free to flex to the 20° flexion angle.

Operation of the brace for fixing the desired extension and flexion angles is accomplished by selecting the appropriate extension angle limit element and flexion angle limit element with base widths providing contact of the limiting surfaces and mating surfaces at the limit angles. With the brace struts at a rotation angle equal to or less than the desired maximum flexion angle, the flexion angle limit element is inserted in the posterior port in the hinge assembly. With the tab received in the posterior recess in the hinge plate to assure that a flexion angle limit element is being installed, the engagement mechanism secures the flexion angle limit element in the posterior port. With the brace struts flexed at or beyond the maximum extension limit angle, the selected extension angle limit element is inserted in the anterior port in the hinge assembly. With the tab received in the anterior recess in the hinge plate to assure that an extension angle limit element is being installed, the engagement mechanism secures the extension angle limit element in the anterior port. The angle limit elements may be removed and replaced, without removal of the brace from the patient if desired, by adjusting the flexion/extension angle of the struts to relax pressure between the limiting surfaces on the angle limit elements and mating surfaces on the struts and disengaging the engagement mechanism for the angle limit elements as described for the embodiments disclosed. Either or both angle limit elements may then be removed from their ports. A different size angle limit element may then be installed using the insertion procedures previously described.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. An angle limitation system for an orthopedic brace comprising:
   a hinge assembly rotatably receiving an upper strut and a lower strut and having a hinge plate and a hinge assembly cap;
   an extension angle limit element removably insertable in an anterior port between the hinge plate and hinge assembly cap, said extension angle limit element having a body with limiting surfaces adapted to engage mating faces indented in anterior edges of the upper and lower strut;
   a flexion angle limit element removably insertable in a posterior port between the hinge plate and hinge assembly cap, said flexion angle limit element having a body with limiting surfaces adapted to engage mating faces indented in posterior edges of the upper and lower strut; and,
   engagement mechanisms comprising a resilient lever extending from each body, said resilient lever engaged in a mating channel in the hinge assembly cap to prevent extraction of the body from the respective anterior or posterior port, the hinge assembly cap having an aperture extending through the hinge assembly cap into the associated mating channel said aperture receiving a tool inserted to engage the resilient lever whereby depression of the lever by the tool disengages the lever from the mating channel to releasably secure the flexion angle limit element in the posterior port and the extension angle limit element in the anterior port.

2. The angle limitation system for an orthopedic brace as defined in claim 1 wherein the limiting surfaces and the mating faces are shaped to employ mechanical leverage present in rotation of the struts to prevent the extension or flexion angle limit elements from being squeezed out of the anterior or posterior port as the struts reach a constrained extension angle.

3. The angle limitation system for an orthopedic brace as defined in claim 2 further comprising points in the mating faces engaging the limiting surfaces to provide a clamping effect.

4. The angle limitation system for an orthopedic brace as defined in claim 2 further comprising rounded protrusions in the limiting surfaces received in cutouts in the mating faces to provide a clamping effect.

5. The angle limitation system for an orthopedic brace as defined in claim 1 further comprising:
   a first surface tab extending from the extension angle limit element and received in an anterior recess in the hinge plate when the body of the extension angle limit element is received in the anterior port; and
   a second surface tab extending from the flexion angle limit element and received in a posterior recess in the hinge plate when the body of the flexion angle limit element is received in the posterior port between the hinge plate and hinge assembly cap;
   said first and second surface tabs sized to be received only in the anterior recess and posterior recess respectively.

6. The angle limitation system for an orthopedic brace as defined in claim 5 further comprising a relief in each of the anterior recess and posterior recess allowing engagement of the first and second surface tabs for removal of the extension angle limit element and flexion angle limit element.

7. A method for operation of an orthopedic brace comprising:
   selecting an appropriate extension angle limit element and flexion angle limit element with base widths providing contact of limiting surfaces and mating surfaces at desired limit angles;
   rotating an upper strut and a lower strut of a hinge assembly, rotatably receiving the upper strut and the lower strut and having a bin e plate and a hinge assembly cap, to an angle equal to or less than the desired maximum flexion angle;
   inserting the selected flexion angle limit element removably insertable in a posterior port between the hinge plate and hinge assembly cap, said flexion angle limit element having a body with limiting surfaces adapted to engage mating faces indented in posterior edges of the upper and lower strut in the posterior port in the hinge assembly; and,
   releasably securing the flexion angle limit element in the posterior port with an engagement mechanism comprising a first resilient lever extending from the body, said resilient lever engaged in a first mating channel in the hinge assembly cap to prevent extraction of the body from the respective anterior or posterior port, the hinge assembly cap having a first aperture extending through the hinge assembly can into the first mating channel said first aperture receiving a tool inserted to engage the resilient lever whereby depression of the first resilient lever by the tool disengages the first resilient lever from the first mating channel;
   flexing brace struts at or beyond a maximum extension limit angle;
   inserting the selected extension angle limit element removably insertable in an anterior port between the hinge plate and hinge assembly cap, said extension angle limit element having a body with limiting surfaces adapted to engage mating faces indented in anterior edges of the upper and lower strut in the anterior port in the hinge assembly of the brace;
   releasably securing the extension angle limit element in the anterior port with an engagement mechanism comprising a second resilient lever extending from the body, said resilient lever engaged in a second mating channel in the hinge assembly cap to prevent extraction of the body from the respective anterior or posterior port, the hinge assembly cap having a second aperture extending through the hinge assembly cap into the second mating channel said second aperture receiving a tool inserted to engage the resilient lever whereby depression of the first resilient lever by the tool disengages the second resilient lever from the second mating channel.

8. A method for operation of an orthopedic brace as defined in claim 7 further comprising:
   adjusting the flexion/extension angle of the struts to relax pressure between the limiting surfaces on the extension and flexion angle limit elements and mating surfaces on the struts;
   disengaging the engagement mechanism for the extension and flexion angle limit elements; and,
   removing either or both the extension and flexion angle limit elements from the anterior and posterior ports.

9. A method for operation of an orthopedic brace as defined in claim 7 further comprising:
   receiving a first surface tab in a posterior recess in the hinge plate to assure that a flexion angle limit element is being installed, and receiving a second surface tab in an anterior recess in the hinge plate to assure that an extension angle limit element is being installed.

\* \* \* \* \*